United States Patent [19]

Dunn

[11] 3,931,160
[45] Jan. 6, 1976

[54] α-AMINO-α-(ACYLAMIDOPHENYL-)ACETAMIDOCEPHALOSPORINS

[75] Inventor: George L. Dunn, Wayne, Pa.

[73] Assignee: SmithKline Corporation, Philadelphia, Pa.

[22] Filed: May 15, 1974

[21] Appl. No.: 470,233

[52] U.S. Cl............................ 260/243 C; 424/246
[51] Int. Cl.².................................. C07D 501/20
[58] Field of Search .............................. 260/243 C

[56] References Cited
UNITED STATES PATENTS

| 3,464,985 | 9/1969 | Holdrege | 260/243 C |
| 3,776,906 | 12/1973 | Essery et al. | 260/243 C |
| 3,813,388 | 5/1974 | Crast | 260/243 C |
| 3,840,535 | 10/1974 | Kaplan et al. | 260/243 C |

Primary Examiner—Nicholas S. Rizzo
Attorney, Agent, or Firm—Stuart R. Suter; Alan D. Lourie; William H. Edgerton

[57] ABSTRACT

7-[α-Amino-α-(acylamidophenyl)acetamido]-cephalosporins are prepared. They show improved antibacterial activity especially when they are administered orally.

17 Claims, No Drawings

α-AMINO-α-(ACYLAMIDOPHENYL)-ACETAMIDOCEPHALOSPORINS

This invention relates to novel cephalosporins which have antibacterial activity. In particular, the compounds have an acylamidophenylglycinamido moiety at position 7 of the cephem nucleus.

BACKGROUND AND PRIOR ART

A wide variety of semi-synthetic cephalosporins have been prepared and tested since the natural group of cephalosporins were discovered. A most difficult problem within this area is the discovery of cephalosporins which are effective when administered orally. Cephaloglycine, U.S. Pat. No. 3,560,489; cephalexin, U.S. Pat. No. 3,507,861; and cephradine, U.S. Pat. No. 3,485,819 are the only compounds that have had sufficient oral activity to warrant commercial use. We have now discovered a new series of cephalosporins which have oral activity.

The prior art includes U.S. Pat. No. 3,464,985 which discloses compounds with a lower alkanoylamino group substituted at any position on the phenyl ring of cephaloglycine. Also disclosed are similar compounds where the amino and amido nitrogen atoms of the above compounds have been reacted with acetone to give a cyclic system. U.S. Pat. No. 3,634,418 discloses 3-azidomethylcephalosporins containing a lower alkanoylaminophenylglycyl group at position 7. Other cephalosporins containing an alkanoylaminophenyl group are described in U.S. Pat. No. 3,646,024. Phenylglycylcephalosporins having a 3-heterocyclicthiomethyl group are described in U.S. Pat. Nos. 3,641,021; 3,687,948; 3,759,904; 3,757,012; 3,743,644; 3,734,907; and perhaps others which are unknown to me at this time.

SUMMARY OF THE INVENTION

The compounds of this invention are more fully defined by the following formula:

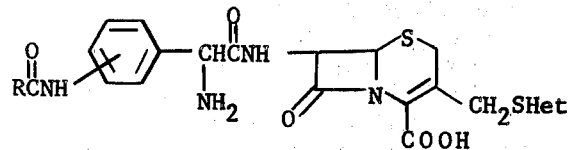

where:
the RCONH group is attached at the para or meta position;
R is hydrogen, lower alkyl of 1–4 carbon atoms, or trifluoromethyl;
Het is a 5 or 6 membered ring containing carbon and 1–4 atoms selected from the group consisting of N, O, and S, unsubstituted or substituted with one or two substituents selected from the group consisting of $C_1-C_6$ alkyl, $C_1-C_6$ alkoxy, allyloxy, oxide, carbamyl, carboxyl, carbalkoxy of $C_1-C_6$, halogen, mercapto, methylthio, trifluoromethyl, hydroxy, amino, alkylamino, and dialkylamino, each undefined alkyl having 1–6 carbon atoms.

Within the definition of Het is included the N-oxide derivatives of the heterocyclic systems named where such derivatives are possible, for example pyridyl-N-oxide.

Preferred compounds are those compounds where Het is tetrazolyl, triazolyl, thiadiazolyl, oxadiazolyl, diazolyl, pyridyl, pyrimidyl and pyrazinyl. Also preferred are compounds where R is hydrogen, methyl, or trifluoromethyl.

Due to the presence of both the amino and carboxylic acid groups, the compounds of this invention can exist in the zwitterion form or as an acid or base salt. These salts in addition to the free form of the compounds are within the scope of this invention. The salts are prepared by standard well-known methods using any one of a variety of known and accepted nontoxic pharmaceutically acceptable acids and bases that are known in the art.

The asymmetric carbon in the acylamidophenylglycine sidechain gives rise to optical isomers of which the diastereomers having the D-configuration in the sidechain are preferred; however, those having the L-configuration or a diastereomeric mixture in the sidechain are within the scope of the invention.

The compounds of this invention are prepared by acylation of a 7-aminocephem nucleus with the appropriate substituent at position 3 with the appropriate p-acylamidophenylglycine. To effect the acylation, the glycine carboxylic acid group is activated by any of the standard methods such as mixed anhydride, acid chloride or activated ester. In addition, a coupling agent, for example dicyclohexylcarbodiimide, can be used provided that the cephem carboxylic acid group is protected with an easily removable protecting group, for example the t-butyl ester. The glycine amino group must be protected during the acylation. Many protecting groups are known in the art such as t-butoxycarbonyl, trichloroethoxycarbonyl, benzyloxycarbonyl, the methyl acetoacetate adduct or similar groups which have been used in peptide synthesis.

The compounds may alternatively be prepared by acylating 7-aminocephalosporanic acid (7-ACA) with the N-protected acylamidophenylglycine and then displacing the acetoxy group with the desired heterocyclicthiol. Removal of the protecting group by standard methods gives the product compounds of this invention.

The starting materials for the compounds of this invention are known, prepared by known methods or described herein. The acylamidophenylglycines are prepared by acylating p-aminophenylglycine and m-aminophenylglycine (U.S. Pat. No. 3,479,339) after first protecting the glycine amino group with a protecting group such as those described above. The acylating agents of formic acid, the $C_1-C_4$ alkanoic acids and trifluoroacetic acid are well known in the art. The 7-amino-3-heterocyclicthiomethyl-3-cephem-4-carboxylic acids are prepared by displacing the acetoxy group of 7-ACA with a heterocyclicthiol by the method described in U.S. Pat. No. 3,516,997. The t-butyl esters are also prepared by standard methods.

The compounds have antibacterial activity against both Gram-positive and Gram-negative organisms and are therefore useful for the treatment or prevention of bacterial infections. The antibacterial activity is observed in animals when the compounds are administered either orally or parenterally. Minimum inhibitory concentrations (MIC) were determined using the standard tube dilution method. MICs ranged from 1.6 to greater than 200 μg/ml when tested against a variety of bacteria. The in vivo activity in animals of the compounds of this invention was determined by administering the compounds to mice infected with E. coli and Kleb. pneumonia. The results of the tests obtained from both oral and subcutaneous administration of compounds of this invention and a standard, cephalexin, are reported in Table 1 as $ED_{50}$ in mg/kg.

TABLE 1

| Compound* | E. coli | | K. pneumo | |
|---|---|---|---|---|
| | sc | po | sc | po |
| 1 | 4.2 | 8.5 | 5.5 | 12.5 |
| 2 | <3 | 35 | 12.5 | >25 |
| 3 | 4.5 | 18 | 6.2 | 6.2 |
| 4 | 1.5 | 3.5 | 1.5 | 2.2 |
| Cephalexin | 17.5 | 17.5 | 50 | 22 |

*See Table 2 for structures

TABLE 2

| Com- pound | R | A |
|---|---|---|
| 1 | p-methyl | 5-methyl-1,3,4-thiadiazol-5-ylthio |
| 2 | p-methyl | 1-methyltetrazol-5-ylthio |
| 3 | p-CF$_3$ | 5-methyl-1,3,4-thiadiazol-5-ylthio |
| 4 | p-hydrogen | 5-methyl-1,3,4-thiadiazol-5-ylthio |

The compounds are formulated into pharmaceutical compositions in the same manner as other cephalosporins. They are administered parenterally as sterile aqueous solutions or orally as tablets, capsules or suspensions. The amount given varies with age, size and condition of the subject as well as the severity of the infection and can be determined by one skilled in the art. The dosage in general ranges from 250 to 1000 mg while the daily dosage, which may be divided, may range from one to 5 grams.

The following examples are presented to illustrate the invention but are not to be viewed as limiting the scope thereof.

PREPARATION 1

D(−)-α-t-Butoxycarboxamido-α-(p-formamidophenyl)acetic acid

A mixture of D(−)-α-t-butoxycarboxamido-α-(p-aminophenyl)acetic acid (2.84 g, 0.01 mol) and acetic-formic anhydride (0.01 mol) was stirred for one hour. The solid product was collected and washed with acetone and ether.

PREPARATION 2

D(−)-α-t-butoxycarboxamido-α-(p-trifluoroacetamidophenyl)-acetic acid

The pH of a suspension of D(−)-α-t-butoxycarboxamido-α-(p-aminophenyl)acetic acid (5.4 g) was adjusted to 9.5 with 1N NaOH to effect solution. Ethyl trifluorothioacetate (8.0 ml) was added and the reaction was stirred at room temperature for 23hours during which time the pH was maintained at 9–9.5 by the addition of NaOH as needed. The solution was acidified to pH 1 with 3N HCl and the product was collected and dried.

PREPARATION 3

α-t-Butoxycarboxamido-α-(p-acetamidophenyl)acetic acid

D(−)-α-t-Butoxycarboxamido-α-(p-aminophenyl)-acetic acid hydrate (6.73 g) was dissolved in glacial acetic acid (60 ml) and acetic anhydride (4.52 ml) was added to the solution. The reaction was stirred at room temperature for 2 hours and then evaporated in vacuo. The residue was dissolved in ethyl acetate and the solution was washed with water, dried and evaporated to give the product.

PREPARATION 4

When D(−)-α-t-butoxycarboxamido-α-(m-aminophenyl)acetic acid is reacted with acetic-formic anhydride, ethyl trifluorothioacetate, or acetic anhydride according to Preparation 1, 2, or 3, respectively, D(−)-α-t-butoxycarboxamido-α-(m-formamidophenyl)acetic acid, D(−)-α-t-butoxycarboxamido-α-(m-trifluoroacetamidophenyl)acetic acid, and D(−)-α-t-butoxycarboxamido-α-(m-acetamidophenyl)acetic acid are obtained.

EXAMPLE 1

7-[α-Amino-α-(p-formamidophenyl)acetamido]-3-(5-methyl-1,3,4-thiadiazol-2-ylthiomethyl)-3-cephem-4-carboxylic acid The phenylglycine derivative of Preparation 1 (1.3 g, 4 mmol) was dissolved in dry tetrahydrofuran (25 ml) and triethylamine (0.55 ml) and N-methylmorpholine (3 drops) were added. The solution was cooled to −15°C and isobutyl chloroformate (0.52 g, 4 mmol) was added. The reaction was stirred 30 minutes at −15°C and then a solution of 7-amino-3-(5-methyl-1,3,4-thiadiazol-2-ylthiomethyl)-3-cephem-4-carboxylic acid (1.53 g, 4 mmol) in a mixture of 50% aqueous tetrahydrofuran (50 ml) and triethylamine (0.55 ml) was added. The solution was stirred without cooling for 3.5 hours. The tetrahydrofuran was removed in vacuo and the residue was diluted with water (50 ml) and extracted with ethyl acetate. The aqueous solution was acidified with 3N HCl to pH 1 and extracted with ethyl acetate. The extracts were dried and evaporated to about half volume. On standing crystals formed which were collected, washed with ether and dried; 1.5 g. The solid was added to a cold solution (0°C) of trifluoroacetic acid (15 ml) and anisole (1.5 ml) and stirred for 15 minutes. The solution was evaporated under vacuum and the trifluoroacetate salt was triturated with ether and collected. The salt was dissolved in water and stirred with a basic polystyrene ion-exchange resin ("Amberlite IR-45") until pH 5.7 was reached. After filtration the aqueous solution was freeze dried to give the product.

EXAMPLE 2

7-[α-Amino-α-(p-formamidophenyl)acetamido]-3-(1,2,3-triazol-4-ylthiomethyl)-3-cephem-4-carboxylic acid When 7-amino-3-(1,2,3-triazol-4-ylthiomethyl)-3-cephem-4-carboxylic acid (2.18 g) was reacted with the product of Preparation 1 (2.05 g) according to the procedure of Example 1, the product was obtained which was purified by stirring with THF (25 ml), filtering any insoluble material, and precipitating the product by the addition of hexane.

EXAMPLE 3

7-[α-Amino-α-(p-acetamidophenyl)acetamido]-3-(5-methyl-1,3,4-thiadiazol-2-ylthiomethyl)-3-cephem-4-carboxylic acid t-Butyl 7-amino-3-(5-methyl-1,3,4-thiadiazol-2-ylthiomethyl)-3-cephem-4-carboxylate (2.4 g, 6 mmol) was dissolved in THF (35 ml). Dicyclohexylcarbodiimide (0.99 g, 4.8 mmol) was added to the solution followed by the acetic acid product from Preparation 3 (2.1 g, 13% excess due to solvation of ethyl acetate). The reaction was stirred for two hours, the solid urea was collected, and the filtrate was evaporated. The residue was dissolved in ether-ethyl acetate and added to a large volume of petroleum ether. The semi-solid product was collected and dissolved in ethyl acetate. The solution was washed with 1.5N HCl, 5% NaHCO₃, and water; dried over MgSO₄; and evaporated to give the protected product. This solid was stirred for one hour in cold trifluoroacetic acid (15 ml) and then the solution was evaporated to dryness under high vacuum. The residue was triturated with ether, collected and then dissolved in water and stirred with basic ion-exchange resin ("Amberlite IR-45") until pH 4.5 was obtained. The resin was removed and the aqueous solution was freeze dried to give the product.

EXAMPLE 4

7-[α-Amino-α-(p-acetamidophenyl)acetamido]-3-(1-methyltetrazol-5-ylthiomethyl)-3-cephem-4-carboxylic acid The title compound was obtained when 7-amino-3-(1-methyltetrazol-5-ylthiomethyl)-3-cephem-4-carboxylic acid (3.44 g) was acylated with the acetic acid of Preparation 3 (3.17 g, 0.01 mol) using the mixed anhydride method of Example 1. The t-butyoxy carbonyl protected product was chromatographed prior to deblocking on a silica gel column using 80:20:10 chloroform: isopropanol: formic acid as eluant.

EXAMPLE 5

7-[α-Amino-α-(p-trifluoroacetamidophenyl)acetamido]-3-(5-methyl-1,3,4-thiadiazol-2-ylthiomethyl)-3-cephem-4-carboxylic acid To a suspension of t-butyl 7-amino-3-(5-methyl-1,3,4-thiadiazol-2-ylthiomethyl)-3-cephem-4-carboxylate hydrochloride (0.874 g, 2 mmol) in tetrahydrofuran (50 ml) was added triethylamine (0.28 ml, 2 mmol). To this solution was added the acetic acid of Preparation 2 (0.724 g, 2 mmol) in tetrahydrofuran (10 ml) followed by dicyclohexylcarbodiimide (0.425 g) in tetrahydrofuran (5 ml). The reaction solution was stirred for 3.5 hours at room temperature and then the solid urea was filtered off. The filtrate was evaporated to a residue which was dissolved in ethyl acetate. The solution was filtered, washed with 3N HCl, water, 5% NaHCO₃ and water and then dried and evaporated. The solid was dissolved in a mixture of ether and tetrhydrofuran and then precipitated by the addition of hexane. This solid (530 mg) was added to cold trifluoroacetic acid and stirred one hour without additional cooling. The solution was evaporated and then triturated with ether to give the trifluoroacetate salt which was treated with ion-exchange resin as previously described to give the title product.

EXAMPLE 6

Substitution of 7-amino-3-(1-methyltetrazol-5-ylthiomethyl)-3-cephem-4-carboxylic acid for 7-amino-3-(5-methyl-1,3,4-thiadiazol-2-ylthiomethyl)-3-cephem-4-carboxylic acid in the procedure of Example 1 gives
  7-[α-amino-α-(p-formamidophenyl)-acetamido]-3-(1-methyltetrazol-2-ylthiomethyl)-3-cephem-4-carboxylic acid.

EXAMPLE 7

7-Amino-3-(1,2,3-triazol-4-ylthiomethyl)-3-cephem-4-carboxylic acid is acylated with D(−)-α-t-butoxycarboxamido-α-(p-trifluoroacetamidophenyl)acetic acid or D(−)-α-t-butoxycarboxamido-α-(p-acetamidophenyl)acetic acid using the mixed anhydride procedure of Example 1 to give the following products:
  7-[α-amino-α-(p-trifluoroacetamido-phenyl)acetamido]-3-(1,2,3-triazol-4-ylthiomethyl)-3-cephem-4-carboxylic acid
  7-[α-amino-α-(p-acetamidophenyl)acetamido]-3-(1,2,3-triazol-4-ylthiomethyl)-3-cephem-4-carboxylic acid.

EXAMPLE 8

Substitution of the t-butyl ester of 7-amino-3-(1-methyltetrazol-5-ylthiomethyl)-3-cephem-4-carboxylic acid into the procedure of Example 5 for t-butyl 7-amino-3-(5-methyl-1,3,4-thiadiazol-2-ylthiomethyl)-3-cephem-4-carboxylic acid gives
  7-[α-amino-α-(p-trifluoroacetamidophenyl)acetamido]-3-(1-methyltetrazol-5-ylthiomethyl)-3-cephem-4-carboxylic acid

EXAMPLE 9

When an equimolar amount of the following 7-amino-3-heterocyclicthiomethyl-3-cephem-4-carboxylic acids are substituted for 7-amino-3-(5-methyl-1,3,4-thiadiazol-2-ylthiomethyl)-3-cephem-4-carboxylic acid in the procedure of Example 1, the corresponding 7-[α-amino-α-(p-formamidophenyl)acetamido]-3-heterocyclicthiomethyl-3-cephem-4-carboxylic acid is formed.
  7-Amino-3-(tetrazol-5-ylthiomethyl)-3-cephem-4-carboxylic acid
  7-Amino-3-(1,3,4-thiadiazol-2-ylthiomethyl)-3-cephem-4-carboxylic acid
  7-Amino-3-(5-trifluoromethyl-1,3,4-thiadiazol-2-ylthiomethyl)-3-cephem-4-carboxylic acid
  7-Amino-3-(5-ethyl-1,3,4-thiadiazol-2-ylthiomethyl)-3-cephem-4-carboxylic acid
  7-Amino-3-(5-n-butyl-1,3,4-thiadiazol-2-ylthiomethyl)-3-cephem-4-carboxylic acid
  7-Amino-3-(5-dimethylamino-1,3,4-thiadiazol-2-ylthiomethyl)-3-cephem-4-carboxylic acid
  7-Amino-3-(5-mercapto-1,3,4-thiadiazol-2-ylthiomethyl)-3-cephem-4-carboxylic acid
  7-Amino-3-(3-methylthio-1,2,4-thiadiazol-5-ylthiomethyl)-3-cephem-4-carboxylic acid
  7-Amino-3-(3-methyl-1,2,4-thiadiazol-5-ylthiomethyl)-3-cephem-4-carboxylic acid
  7-Amino-3-(1,2,4-triazol-3-ylthiomethyl)-3-cephem-4-carboxylic acid
  7-Amino-3-(5-methyl-1,2,4-triazol-3-ylthtiomethyl)-3-cephem-4-carboxylic acid
  7-Amino-3-(4-methyl-1,2,4-triazol-3-ylthiomcthyl)-3-cephem-4-carboxylic acid 7-Amino-3-(4,5-dimethyl-1,2,4-triazol-3-ylthiomethyl)-3-cephem-4-carboxylic acid
7-Amino-3-(2,5-dimethyl-1,2,4-triazol-3-ylthiomethyl)-3-cephem-4-carboxylic acid
7-Amino-3-(4-methyl-5-trifluoromethyl-1,2,4-triazol-3-ylthiomethyl)-3-cephem-4-carboxylic acid
7-Amino-3-(5-ethyl-1,2,4-triazol-3-ylthiomethyl)-3-cephem-4-carboxylic acid
7-Amino-3-(4-ethyl-1,2,4-triazol-3-ylthiomethyl)-3-cephem-4-carboxylic acid
7-Amino-3-(1-methyl-1,2,4-triazol-5-ylthiomethyl)-3-cephem-4-carboxylic acid
7-Amino-3-(1-methyl-1,2,4-triazol-3-ylthiomethyl)-3-cephem-4-carboxylic acid
7-Amino-3-(1-ethyl-1,2,4-triazol-5-ylthiomethyl)-3-cephem-4-carboxylic acid
7-Amino-3-(1-ethyl-1,2,4-triazol-3-ylthiomethyl)-3-cephem-4-carboxylic acid
7-Amino-3-(4-allyl-1,2,4-triazol-3-ylthiomethyl)-3-cephem-4-carboxylic acid
7-Amino-3-(5-methoxymethyl-1,2,4-triazol-3-ylthiomethyl)-3-cephem-4-carboxylic acid
7-Amino-3-(5-cyclopropyl-1,2,4-triazol-3-ylthiomethyl)-3-cephem-4-carboxylic acid
7-Amino-3-(5-bromo-1,2,4-triazol-3-ylthiomethyl)-3-cephem-4-carboxylic acid
7-Amino-3-(5-hydroxy-4-methyl-1,2,4-triazol-3-ylthiomethyl)-3-cephem-4-carboxylic acid
7-Amino-3-(5-hydroxy-4-ethyl-1,2,4-triazol-3-ylthiomethyl)-3-cephem-4-carboxylic acid
7-Amino-3-(5-hydroxy-1,2,4-triazol-3-ylthiomethyl)-3-cephem-4-carboxylic acid
7-Amino-3-(1-methyl-1,2,3-triazol-5-ylthiomethyl)-3-cephem-4-carboxylic acid
7-Amino-3-(4-methyl-1,2,3-triazol-5-ylthiomethyl)-3-cephem-4-carboxylic acid
7-Amino-3-(1,3,4-oxadiazol-2-ylthio-methyl)-3-cephem-4-carboxylic acid
7-Amino-3-(5-methyl-1,3,4-oxadiazol-2-ylthiomethyl)-3-cephem-4-carboxylic acid
7-Amino-3-(4-pyrimidylthiomethyl)-3-cephem-4-carboxylic acid
7-Amino-3-(2-pyrazinylthiomethyl)-3-cephem-4-carboxylic acid
7-Amino-3-(3-pyridylthiomethyl)-3-cephem-4-carboxylic acid
7-Amino-3-(4-pyridylthiomethyl)-3-cephem-4-carboxylic acid
7-Amino-3-(1-oxide-2-pyridylthiomethyl)-3-cephem-4-carboxylic acid.

EXAMPLE 10

When a t-butyl ester of any 7-amino-3-heterocyclicthiomethyl cephem compound enumerated in Example 9 is acylated with α-t-butoxycarboxamido-α-(p-trifluoroacetamidophenyl)acetic acid according to the procedure of Example 5, the corresponding 7-[α-amino-α-(p-trifluoroacetamidophenyl)acetamido]-3-heterocyclicthiomethyl-3-cephem-4-carboxylic acid, is obtained.

EXAMPLE 11

Acylation of any 7-amino-3-heterocyclicthiomethyl cephem compound enumerated in Example 9 with α-t-butoxycarboxamido-α-(p-acetamidophenyl)acetic acid according to the procedure of Example 1 gives the desired 7-[α-amino-α-(p-acetamidophenyl)acetamido-3-heterocyclicthiomethyl-3-cephem-4-carboxylic acid.

EXAMPLE 12

The 7-[α-amino-α-(m-acylamidophenyl)acetamido]-cephalosporins are prepared by substituting the corresponding α-t-butoxycarboxamido-α-(m-acylamidophenyl)acetic acid for the α-t-butoxycarboxamido-α-(p-acylamidophenyl)acetic acid in each procedure of Examples 1–11.

Representative compounds prepared within this example include the following:

7-[α-amino-α-(m-formamidophenyl)-acetamido]-3-(1-methyltetrazol-5-ylthiomethyl)-3-cephem-4-carboxylic acid 7-[α-amino-α-(m-formamidophenyl)-acetamido]-3-(5-methyl-1,3,4-thiadiazol-2-ylthiomethyl)-3-cephem-4-carboxylic acid 7-[α-amino-α-(m-formamidophenyl)acet-amido]-3-(1,2,3-triazol-4-ylthio-methyl)-3-cephem-4-carboxylic acid 7-[α-amino-α-(m-acetamidophenyl)-acetamido]-3-(1-methyltetrazol-5-ylthiomethyl)-3-cephem-4-carboxylic acid 7-[α-amino-α-(m-acetamidophenyl)-acetamido]-3-(5-methyl-1,3,4-thiadiazol-2-ylthiomethyl)-3-cephem-4-carboxylic acid 7-[α-amino-α-(m-acetamidophenyl)-acetamido]-3-(1,2,3-triazol-4-ylthiomethyl)-3-cephem-4-carboxylic acid 7-[α-amino-α-(m-trifluoroacetamido-phenyl)acetamido]-3-(1-methyltetrazol-5-ylthiomethyl)-3-cephem-4-carboxylic acid 7-[α-amino-α-(m-trifluoroacetamidophenyl)acetamido]-3-(5-methyl-1,3,4-thiadiazol-2-ylthiomethyl)-3-cephem-4-carboxylic acid 7-[α-amino-α-(m-trifluoroacetamidophenyl)acetamido]-3-(1,2,3-triazol-4-ylthiomethyl)-3-cephem-4-carboxylic acid.

EXAMPLE 13

An injectable pharmaceutical composition is prepared by dissolving 500 mg of sodium 7-[α-amino-α-(p-formamidophenyl)acetamido]-3-(5-methyl-1,3,4-thiadiazol-2-ylthiomethyl)-3-cephem-4-carboxylate in sterile water or sterile normal saline solution (1–2 ml). The other compounds of this invention are formulated in a similar manner.

An antibacterial capsule is comprised of the following components:

| | |
|---|---|
| cephalosporin | 500 mg. |
| lactose | 250 mg. |
| magnesium stearate | 75 mg. |

I claim:
1. A compound of the formula

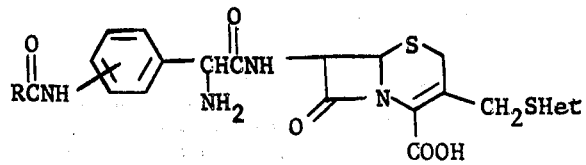

wherein:
the RCONH group is attached at the para or meta positions;

R is hydrogen, lower alkyl of 1–4 carbon atoms, or trifluoromethyl; and

Het is a 5 or 6 member heterocyclic ring containing carbon and 1–4 atoms selected from the group consisting of N, O, and S, unsubstituted or substituted with one or two substituents selected from the group consisting of $C_1$–$C_6$ alkyl, $C_1$–$C_6$ alkoxy, allyoxy, oxide, carbamyl, carboxyl, carbalkoxy of $C_1$–$C_6$, halogen, mercapto, methylthio, trifluoromethyl, hydroxy, amino, alkylamino and dialkylamino, each undefined alkyl having 1–6 carbon atoms, or a non-toxic pharmaceutically acceptable salt thereof.

2. A compound as claimed in claim 1 in which the RCONH group is attached at the para position.

3. A compound as claimed in claim 2 where Het is tetrazolyl, thiadiazolyl, triazolyl, oxadiazolyl, diazolyl, pyridyl, pyrimidyl or pyrazinyl, unsubstituted or substituted with one or two lower alkyl groups containing 1–4 carbon atoms.

4. A compound as claimed in claim 3 where R is hydrogen.

5. A compound as claimed in claim 3 where R is lower alkyl of 1–4 carbon atoms.

6. A compound as claimed in claim 3 where R is trifluoromethyl.

7. A compound as claimed in claim 5 where R is methyl.

8. A compound as claimed in claim 4 being the compound 7-[α-amino-α-(p-formamidophenyl)acetamido]-3-(5-methyl-1,3,4-thiadiazol-2-ylthiomethyl)-3-cephem-4-carboxylic acid.

9. A compound as claimed in claim 4 being the compound 7-[α-amino-α-(p-formamidophenyl)acetamido]-3-(1,2,3-triazol-4-ylthiomethyl)-3-cephem-4-carboxylic acid.

10. A compound as claimed in claim 6 being the compound 7-[α-amino-α-(p-trifluoroacetamidophenyl)-acetamido]-3-(5-methyl-1,3,4-thiadiazol-2-ylthiomethyl)-3-cephem-4-carboxylic acid.

11. A compound as claimed in claim 7 being the compound 7-[α-amino-α-(p-acetamidophenyl)acetamido]-3-(5-methyl-1,3,4-thiadiazol-2-ylthiomethyl)-3-cephem-4-carboxylic acid.

12. A compound as claimed in claim 7 being the compound 7-[α-amino-α-(p-acetmidophenyl)acetamido]-3-(1-methyltetrazol-5-ylthiomethyl)-3-cephem-4-carboxylic acid.

13. A compound as claimed in claim 1 in which the RCONH group is attached at the meta position.

14. A compound as claimed in claim 13 where Het is tetrazolyl, thiadiazolyl, triazolyl, oxadiazolyl, diazolyl, pyridyl, pyrimidyl or pyrazinyl, unsubstituted or substituted with one or two lower alkyl groups containing 1–4 carbon atoms.

15. A compound as claimed in claim 14 being the compound 7-[α-amino-α-(m-formamidophenyl)acetamido]-3-(1-methyltetrazol-5-ylthiomethyl)-3-cephem-4-carboxylic acid.

16. A compound as claimed in claim 14 being the compound 7-[α-amino-α-(m-formamidophenyl)acetamido]-3-(5-methyl-1,3,4-thiadiazol-2-ylthiomethyl)-3-cephem-4-carboxylic acid.

17. A compound as claimed in claim 14 being the compound 7-[α-amino-α-(m-formamidophenyl)acetamido]-3-(1,2,3-triazol-4-ylthiomethyl)-3-cephem-4-carboxylic acid.

* * * * *